(12) United States Patent
Birger et al.

(10) Patent No.: US 9,909,955 B2
(45) Date of Patent: Mar. 6, 2018

(54) USES OF HYDROPHOBIC AGGREGATES AND METHODS FOR PERFORMING THOSE USES

(71) Applicants: Zeev Birger, Ramat Hasharon (IL); Yoram Hasson, Ramat Hasharon (IL); Brian David Cohen, Ashkelon (IL); Alon Rosenberg, Rehovot (IL)

(72) Inventors: Zeev Birger, Ramat Hasharon (IL); Yoram Hasson, Ramat Hasharon (IL); Brian David Cohen, Ashkelon (IL); Alon Rosenberg, Rehovot (IL)

(73) Assignee: Coastline Global, Inc., Palo Alto, CA (US)

( * ) Notice: Subject to any disclaimer, the term of this patent is extended or adjusted under 35 U.S.C. 154(b) by 0 days.

(21) Appl. No.: 14/065,128

(22) Filed: Oct. 28, 2013

(65) Prior Publication Data

US 2014/0047933 A1 Feb. 20, 2014

Related U.S. Application Data

(62) Division of application No. 13/147,571, filed as application No. PCT/IB2010/050434 on Feb. 1, 2010.

(60) Provisional application No. 61/149,170, filed on Feb. 2, 2009.

(51) Int. Cl.
| | |
|---|---|
| *A01K 1/01* | (2006.01) |
| *A01K 1/015* | (2006.01) |
| *G01N 1/10* | (2006.01) |
| *A01G 1/08* | (2006.01) |
| *A01G 17/00* | (2006.01) |
| *B01D 24/20* | (2006.01) |
| *B01D 39/02* | (2006.01) |
| *C02F 1/28* | (2006.01) |

(52) U.S. Cl.
CPC ............. *G01N 1/10* (2013.01); *A01G 1/08* (2013.01); *A01G 17/00* (2013.01); *A01K 1/0152* (2013.01); *A01K 1/0107* (2013.01); *A01K 1/0154* (2013.01); *A01K 1/0155* (2013.01); *B01D 24/20* (2013.01); *B01D 39/02* (2013.01); *B01D 2239/0428* (2013.01); *C02F 1/281* (2013.01); *G01N 2001/1031* (2013.01)

(58) Field of Classification Search
None
See application file for complete search history.

(56) References Cited

U.S. PATENT DOCUMENTS 4,326,481 A * 4/1982 Gruss ........................... 119/171
4,471,717 A * 9/1984 Lander ........................ 119/171
(Continued)

OTHER PUBLICATIONS

Cat World, "Obtaining a urine sample" Forum Discussion, Dec. 18, 2006, available at <http://www.cat-world.com.au/forums/index.php?/topic/43027-obtaining-a-urine-sample/>, accessed Jul. 26, 2017, 3 pages.*

*Primary Examiner* — Katherine Zalasky
(74) *Attorney, Agent, or Firm* — Mark David Torche; Patwrite Law

(57) ABSTRACT

A method of collecting a urine sample including appropriately locating hydrophobic sand with respect to the urine sample. Use of the hydrophobic sand including providing a barrier in the form of at least one layer of the sand; and collecting a urine sample by appropriately locating the sand with respect to the urine.

6 Claims, 1 Drawing Sheet

(56) References Cited

U.S. PATENT DOCUMENTS

2002/0073928 A1* 6/2002 Ingman et al. ............... 119/165
2005/0109697 A1* 5/2005 Olivier .......................... 210/610

* cited by examiner

USES OF HYDROPHOBIC AGGREGATES AND METHODS FOR PERFORMING THOSE USES

CROSS REFERENCE TO RELATED APPLICATIONS

This application is a divisional application of U.S. Ser. No. 13/147,571, which claims priority from U.S. provisional patent application 61/149,170, entitled "USES OF HYDROPHOBIC AGGREGATES AND METHODS FOR PERFORMING THOSE USES", which was filed on Feb. 2, 2009. This application is a national stage entry of International application PCT/IB2010/050434, entitled "USES OF HYDROPHOBIC AGGREGATES AND METHODS FOR PERFORMING THOSE USES", which was filed on Feb. 1, 2009, the entire contents of which are incorporated herein by reference.

FIELD OF THE INVENTION

The present invention relates to uses of hydrophobic aggregates and methods for performing those uses.

BACKGROUND OF THE INVENTION

Tree roots in search of water can grow and expand to the point where they can damage adjacent underground objects and structures such as underground piping, sidewalks, driveways, buildings, and so on. Further, the uncontrolled growth of such roots may allow a tree to grow very large, which may be undesirable in an orchard, for example, for reasons of space allocation and ease of picking fruit therefrom, and to help keep tree branches from damaging structures such as buildings and overhead electrical wires.

Urinary and urological ailments in cats are common and require the collection and analysis of one or more urine samples for diagnosis and treatment. Veterinarian extraction of urine samples can be uncomfortable to the cat and stressful for the owner; and is also time consuming and adds expense to the overall treatment.

Containment, collection and remediation of non-polar contaminants, for example, hydrocarbons other chemicals and so on, are ongoing issues considering the ever growing use, transportation and storage of such chemicals. The need for improved and cost effective materials to aid in the containment, collection and remediation is evident by the continued development and expanded use of such materials.

Extinguishing a fire, in particular on water or in wet environments, can be a challenge, in particular in a cost effective environmentally friendly manner. Such fires can occur, for example, at sea, on lakes and ponds, on a road surface or at an industrial site.

Accordingly, it is an object of the present invention to provide one or more uses of hydrophobic particulates or aggregates: as a barrier to control the expansion of tree roots; and/or for the collection of a urine sample and as cat litter and the like; and/or as an aid in the remediation of non-polar contamination (e.g. chemical or hydrocarbon spills); and/or as a fire extinguishing material.

It is also an object of the present invention to provide methods for carrying out those uses.

SUMMARY OF THE INVENTION

The present invention relates to uses of hydrophobic particulates and aggregates and methods related thereto. Exemplary embodiments will be described in regard to use as a barrier for the control of tree roots; for the collection of a urine sample and as (or a component of) cat litter or litter such for other pets/animals, and the like; as an aid in the remediation of non-polar liquid spills; and as a fire extinguishing material. Methods for carrying out those uses will also be described, or understood from the aforementioned embodiments.

The term "sand" will be used herein to denote all suitable particulates and aggregates, for example, crushed stones, gravel, waste slag etc.; and the terms "particulates", "aggregates" and "sand" will be used interchangeably.

The term "tree" will be used herein to denote any tree, shrub, plant, flower and the like with underground roots.

The phrase "mitigation of root growth" herein the specification and claims is used to denote the actual growth of the root and/or the direction of growth.

Without limitation, examples of appropriate hydrophobic particulates and aggregates that can be used in the present invention are disclosed in US Patent Application Publication 2006/257643 (to Zeev Birger, assignee: Superseal Ltd.) which is incorporated herein by reference in its entirety.

In accordance with embodiments of one aspect of the present invention there is provided a method of mitigating the growth of roots comprising positioning at least one layer of hydrophobic sand adjacent said roots. In particular embodiments: one of the at least one layers of sand is positioned below the roots (particularly appropriate for plants and other such flora that typically have shallow roots); an aluminum containing compound is added to the sand, in particular to a coating of the sand; and two or more layers are used.

In accordance with other embodiments there is provided a method of collecting a urine sample by appropriately locating hydrophobic sand with respect to the urine sample. In some of those embodiments, the sand is located in a litter box of a cat or other such pet or animal.

In accordance with other embodiments there is provided a method of aiding in the remediation of a non-polar contamination, for example a hydrocarbon, comprising adsorbing the non-polar contamination onto the hydrophobic sand. In particular embodiments, the non-polar contamination is in a wet environment. In other embodiments, the sand is positioned in locations vulnerable to leaks.

In accordance with other embodiments there is provided a method of aiding in extinguishing a fire on burning material by spreading hydrophobic sand on the burning material. In particular embodiments, the non-polar contamination is in a wet environment and the burning material is adsorbed onto the sand and drawn within the wet environment thereby cutting off sufficient oxygen for combustion.

In accordance with embodiments of one aspect of the present invention there are provided uses of hydrophobic sand comprising at least one of the group consisting of: mitigating the growth of roots by providing a barrier in the form of at least one layer of the sand; collecting a urine sample by appropriately locating the sand with respect to the urine; aiding in the remediation of a non-polar contamination by adsorbing the non-polar contamination; and aiding in extinguishing a fire on burning material by spreading the hydrophobic sand on the burning material.

BRIEF DESCRIPTION OF THE DRAWINGS

The invention may be understood upon reading of the following detailed description of non-limiting exemplary embodiments thereof, with reference to the following drawings, in which.

DETAILED DESCRIPTION OF THE INVENTION

Tree roots, and the roots of other plants, typically spread out in order to find a water source. However, without restriction as to the mechanism, placement of a layer or layers of the aggregates to form a hydrophobic barrier can provide an excellent and convenient barrier for root growth and spreading. None-the-less, while the hydrophobic sand will control the growth and/or direction of growth of many plants and trees, certain roots are particularly rigorous with the capability of travelling relatively great distances in search of nourishment, and will even penetrate hard barriers such as cement walls.

Figure 1:
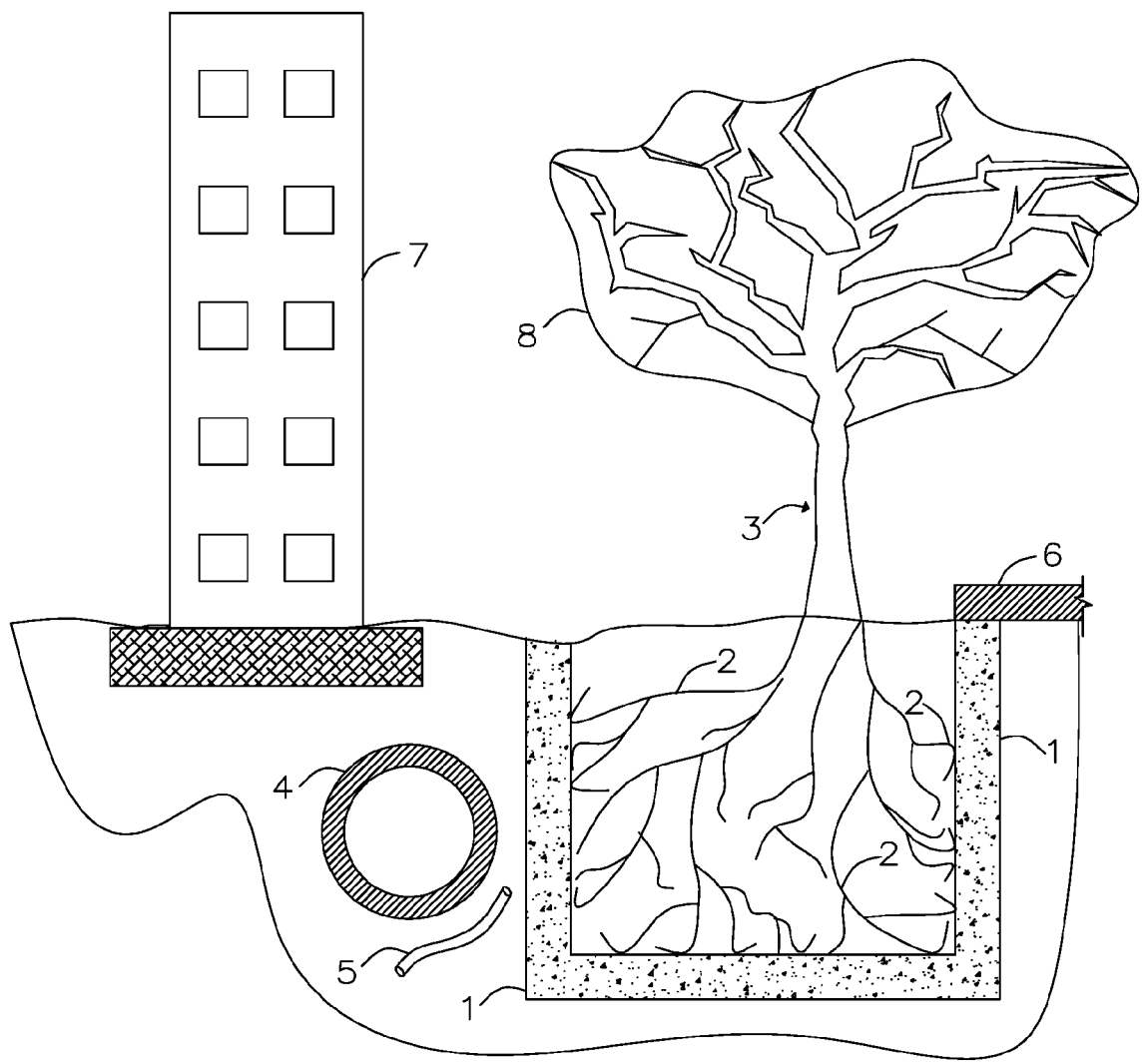
FIG. 1 is a schematic sectional view of an embodiment of a use of hydrophobic aggregates of the present invention as a barrier to help control the expansion of tree roots.

FIG. 1 illustrates an exemplary placement of two hydrophobic sand layers 1 for blocking or containing several roots 2 of a tree 3 from reaching objects to be protected, exemplified by an underground pipe 4, and underground electrical cable 5, a sidewalk 6 and a building 7. It should be understood that the hydrophobic sand layer 1 can be placed in more than one essentially vertical layer(s) or angled layer(s) (e.g. all around the tree 3) and in an essentially horizontal layer (e.g. under the tree 3).

In accordance with particular embodiments of the invention, hydrophobic aggregate layers 1 are disposed inside any of porous panels, fabric, and the like in order to ease installation/application. In other embodiments, hydrophobic aggregate layers 1 comprise a plant or root growth inhibitor.

Advantages of the aforementioned use and method include that they protect objects from root damage in a manner that is cost effective, convenient and are environmentally friendly. Further, there are no other inhibiting effects on the roots 2 and control of root spread can be used to influence the size and shape of the canopy 8 of the tree 3. This is particularly useful for orchards and trees near buildings. In addition, the sand layer 1 is particularly useful for containing and/or diverting irrigation water and nutrients in the area of the roots in order to conserve water and reduce costs. In some embodiments, oil based additives such as root inhibitors can be added to the sand for slow release of the additive in situ.

Man-made hydrophobic sand is coated to repel water. According to some embodiments, chemical(s), in particular aluminum compounds, for example aluminum oxides, silicates or hydroxides, are added to that coating. Roots, such as tree roots 2, react strongly to even very low concentrations of aluminum dioxide, and the addition of such chemicals will tend to reduce the amount of hydrophobic sand, for example in sand layer 1, that is required.

It should be noted that the hydrophobic sand of the hydrophobic sand layer 1 has a relatively low coefficient of friction as it is dry. As such, the sand layer 1 does not provide a good medium for the anchoring or roots 2. Roots tend to seek soil with good anchoring characteristics to stabilize the tree against wind and heavy rain. This is one of the major reasons that roots tend not grow into the hydrophobic sand layer 1.

Further, the hydrophobic sand layer 1 does not provide a friendly environment for micro-organisms, upon which roots depend. This is another reason that the roots 2 do not tend to grow into the hydrophobic sand layer 1.

In addition, most of the vital materials for the tree 3 are drawn to the proximity of roots 2 via normal osmosis in soil. Since hydrophobic sand is completely dry, no such osmosis occurs and consequently, the roots may starve unless turning to seek for normal soil.

In accordance with an embodiment of the present invention, there is provided a use of a hydrophobic aggregate, e.g. sand, for the collection of a urine sample, in particular from a cat; and a use of a hydrophobic aggregate as cat litter.

Figure 2:
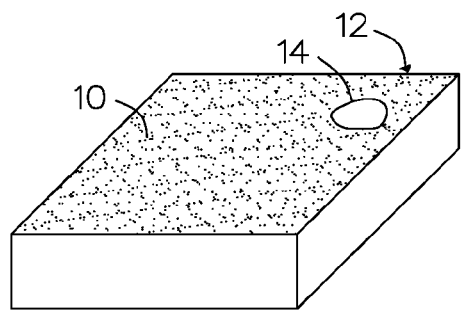
FIG. 2 is a schematic perspective view of an embodiment of a use of hydrophobic aggregates of the present invention for collection of a urine sample and as cat litter.

Referring to FIG. 2, the hydrophobic sand 10 is placed a cat's litter box 12 whose urine is to be tested. When the cat urinates in the box 12 (i.e. on the sand 10), the hydrophobic top layer causes the urine to form into an easily collectible globule 14 on the surface of the sand. Urine from the globule 14 can be conveniently collected, for example, by a syringe or similar utensil (not shown). In accordance with particular embodiments of the invention, hydrophobic sand 10 comprises an anti-bacterial agent for the suppression of smells.

According to another aspect of the invention, related to the aforementioned use, there is provided a method of collecting a urine sample, in particular from a cat, comprising placing at least a layer of hydrophobic sand 10 in a cat box 12, or using the sand as cat litter; and, after a cat whose urine is to be sampled has urinated on the hydrophobic sand, collecting a sample of the urine, for example, by a syringe or the like.

Advantages of the aforementioned use and method include that they are non-invasive, cost effective, convenient, mitigate stress of the cat and owner, an existing litter box can be used, cats will be attracted to urinate on the aggregates as in nature this is generally their medium of choice, the hydrophobic aggregates can be used instead of regular cat litter allowing the advantage of a permanent and continuous observation of the cat's health by the pet owner, if not needed for an analysis sample, the urine globule may be lifted easily removed from the surface of the hydrophobic sand by absorbing with an absorbent cloth or paper (e.g. toilet paper) and discarded, feces on the aggregates can be scooped and disposed of in the usual manner, and the hydrophobic aggregates inhibit the growth of bacterial odors without the use of chemical means, as hydrophobic aggregates do not provide a friendly environment for bacteria.

In accordance with another embodiment of the present invention provides for use of hydrophobic aggregates for the containment and/or collection and/or remediation of non-polar contaminants such as hydrocarbons that have been spilled or leaked. The hydrophobic aggregates adsorb onto hydrocarbons even in a moist or wet environment as the aggregates do not attract the water, rather repel water, due to their hydrophobic nature. In some embodiments, the hydrophobic aggregates are placed in locations vulnerable to leaks, for example under storage tanks and along pipelines, as a preventative measure for to mitigate the spread of any leak and for containment.

Thus, such contaminants can be adsorbed and the sand used to encapsulate an area that has contaminated soil and halt the spread of the contaminant. This allows time for bio-remediation to take place or alternatively allowing for the excavation, transportation and storage of the contaminated soil.

According to a particular embodiment, the hydrophobic aggregates can be impregnated with bio-remediation bacteria, for example a type that remains inert until contact with the hydrocarbons.

The method entails placing one or more layers of hydrophobic aggregates in the path of (or surrounding) the polluted soil. The layers of hydrophobic aggregates can be placed vertically, horizontally or at an angle. According to a specific embodiment, the hydrophobic aggregates can be placed in bags, for example geo-textile bags, which are buried in the soil. These bags can be removed when saturated and replaced with new bags of hydrophobic aggregates.

In order to enhance the absorption process, water can be added to the affected area after the placement of the hydrophobic aggregates.

In this regard, according to further embodiments, the sand is particularly useful in cleaning (adsorbing) oils spills on road surfaces, in particular wet road surfaces, for example, after a traffic accident. One of the advantages with using the hydrophobic sand is that the non-polar contaminant tends to strongly adsorb so that there is no further contamination by dripping or run-off from the sand, and it is convenient to use.

A major advantage of the use and method of this embodiment is that the hydrophobic aggregates are an effective adsorption and barrier material even in wet environments, and poses no collateral detriment to the soil or environment.

According to another embodiment, there is provided a use of hydrophobic aggregates as a fire extinguishing material. Without limitation, this use is particularly applicable to extinguishing burning hydrocarbons (e.g. oil), on a water surface. Such a phenomenon may occur at sea, lakes and ponds, and on road surfaces, for example. The use is accomplished by spreading the hydrophobic sand on the fire, which adsorbs to the hydrocarbon "fuel" and thus separates it from oxygen to thereby extinguish the fire. Typically this occurs by as a result of the hydrophobic sand with the adsorbed hydrocarbon(s) sinking below the water whereby the fire/combustion becomes oxygen starved. According to some embodiments, the hydrophobic aggregates comprise a fire retardant.

Again, the aforementioned use and method provide a cost effective and environmentally friendly solution to the problem.

It should be understood that the above description is merely exemplary and that there are various embodiments of the present invention that may be devised, *mutatis mutandis*, and that the features described in the above-described embodiments may be used separately or in any suitable combination; or the invention can be devised in accordance with embodiments not necessarily described above.

What is claimed is:

1. A method of collecting a urine sample by appropriately locating a layer of hydrophobic sand with respect to the urine sample wherein a hydrophobic top layer of said layer of hydrophobic sand causes the urine to form into a globule that rests on a top surface of the layer of hydrophobic sand; and collecting the urine sample from said globule resting on said top surface of the layer of hydrophobic sand.

2. The method of claim 1, wherein the hydrophobic sand is located in a litter box.

3. The method of claim 1, wherein the collecting comprises using a syringe.

4. Use of hydrophobic sand comprising:
   providing a barrier to urine in the form of a hydrophobic top layer of a layer of said hydrophobic sand, the hydrophobic top layer causing the urine to form into a globule that rests on a top surface of the layer of the hydrophobic sand; and
   collecting a urine sample from said globule of urine resting on the top surface of the layer of said hydrophobic sand.

5. The use of claim 4, wherein collecting a urine sample entails using the hydrophobic sand as animal litter or a component of the litter.

6. The use of claim 4, wherein the collecting comprises using a syringe.

* * * * *